US012582390B2

(12) United States Patent
Ehnholm et al.

(10) Patent No.: US 12,582,390 B2
(45) Date of Patent: Mar. 24, 2026

(54) MECHANICAL WAVE INDUCING DEVICE BEING CONNECTABLE TO A NEEDLE

(71) Applicant: Aalto University Foundation sr, Aalto (FI)

(72) Inventors: Gösta Ehnholm, Aalto (FI); Matti Mikkola, Aalto (FI); Yohann Le Bourlout, Aalto (FI); Heikki J. Nieminen, Aalto (FI)

(73) Assignee: Aalto University Foundation sr, Aalto (FI)

( * ) Notice: Subject to any disclaimer, the term of this patent is extended or adjusted under 35 U.S.C. 154(b) by 1156 days.

(21) Appl. No.: 17/614,002

(22) PCT Filed: May 22, 2020

(86) PCT No.: PCT/FI2020/050345
§ 371 (c)(1),
(2) Date: Nov. 24, 2021

(87) PCT Pub. No.: WO2020/240084
PCT Pub. Date: Dec. 3, 2020

(65) Prior Publication Data
US 2022/0233180 A1     Jul. 28, 2022

(30) Foreign Application Priority Data
May 24, 2019     (FI) ...................................... 20195433

(51) Int. Cl.
*A61B 10/02*        (2006.01)
*A61B 10/04*        (2006.01)
(Continued)

(52) U.S. Cl.
CPC .. *A61B 10/0233* (2013.01); *A61B 2010/0208* (2013.01)

(58) Field of Classification Search
CPC ........ G16H 50/20; G16H 50/30; G16H 50/50; G16H 20/00; A61B 5/446; A61B 5/7267;
(Continued)

(56) References Cited

U.S. PATENT DOCUMENTS

| | | | |
|---|---|---|---|
| 6,702,761 B1 | 3/2004 | Damadian et al. | |
| 2010/0004558 A1 | 1/2010 | Frankhouser et al. | |

(Continued)

FOREIGN PATENT DOCUMENTS

| | | | |
|---|---|---|---|
| GB | 2367895 A | 4/2002 | |
| GB | 2566532 A | 3/2019 | |

(Continued)

*Primary Examiner* — Justin Xu
(74) *Attorney, Agent, or Firm* — Laine IP Oy

(57) ABSTRACT

The inventive device is a mechanical wave inducing device being connectable to a needle. The device has a displacement source and a driving signal connection part in order to connect the displacement source to a signal source. The device has also two connections parts, which are connected to the displacement source, and which each wing part has a connection point to be attached with the needle. The wing parts are converters in order to convert longitudinal mechanical wave movement created by the displacement source into transversal mechanical wave movement for the needle, and at least one connection point is designed to match the transversal mechanical waves to the needle.

30 Claims, 5 Drawing Sheets

(51) Int. Cl.

*A61B 17/22*    (2006.01)
  *A61B 17/32*    (2006.01)
  *A61M 37/00*    (2006.01)

(58) Field of Classification Search

CPC ......... G06T 7/0012; G06T 2207/20081; G06T
         2207/20084; G06T 2207/30088

See application file for complete search history.

(56)       References Cited

U.S. PATENT DOCUMENTS

| | | |
|---|---|---|
| 2015/0374348 A1 | 12/2015 | Hingston |
| 2018/0368883 A1 | 12/2018 | Rossa et al. |

FOREIGN PATENT DOCUMENTS

| | | |
|---|---|---|
| WO | WO2010047734 A1 | 4/2010 |
| WO | WO2018000102 A1 | 1/2018 |

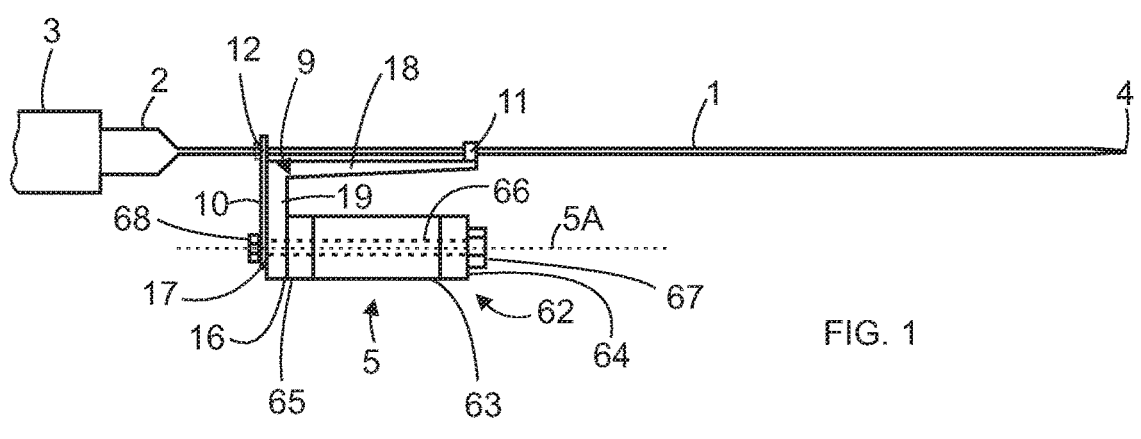
FIG. 1
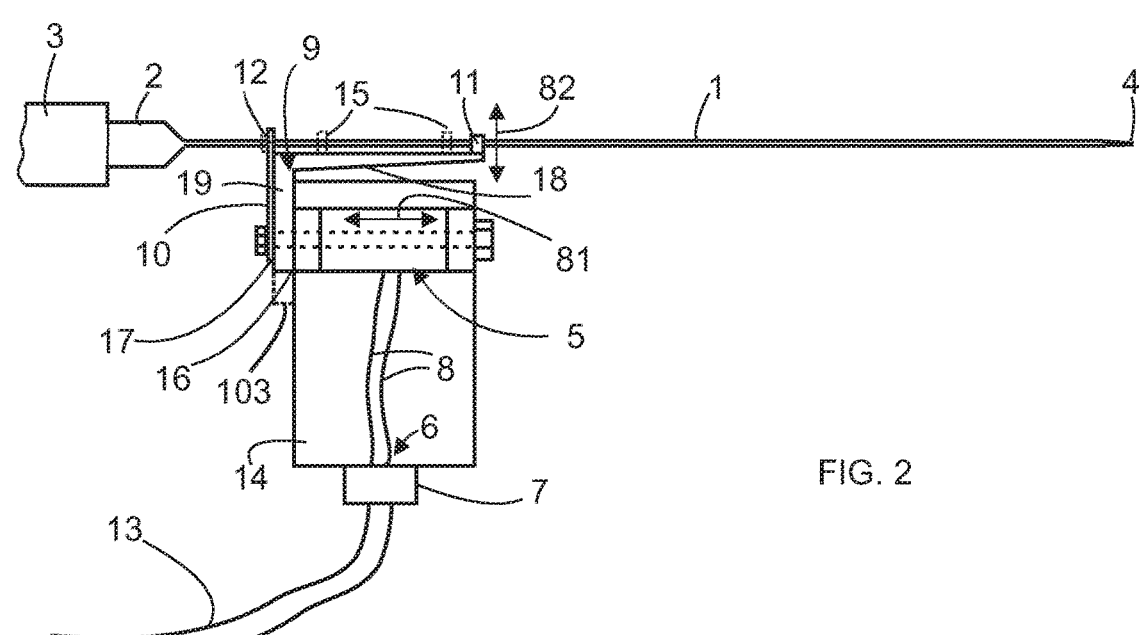
FIG. 2
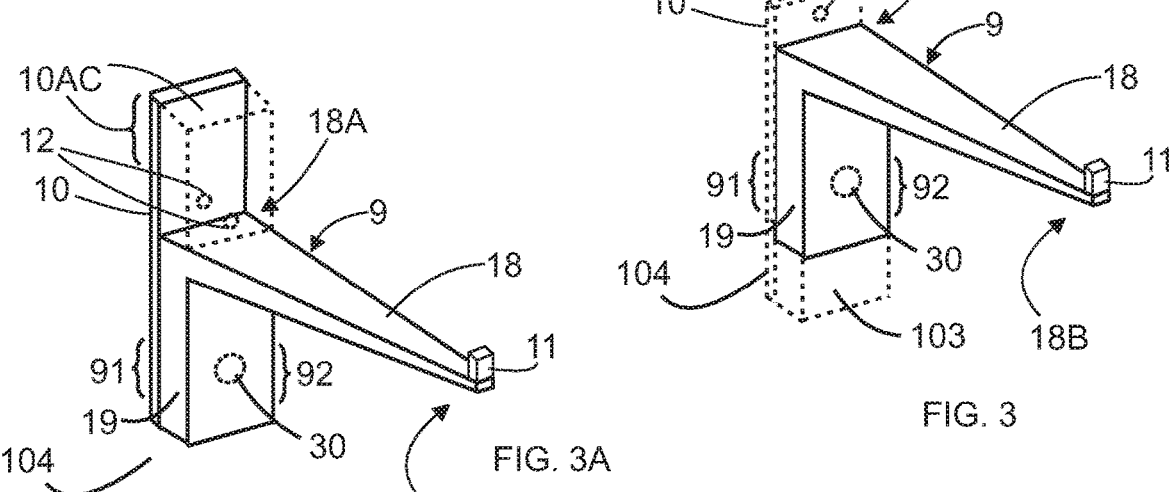
FIG. 3A
FIG. 3

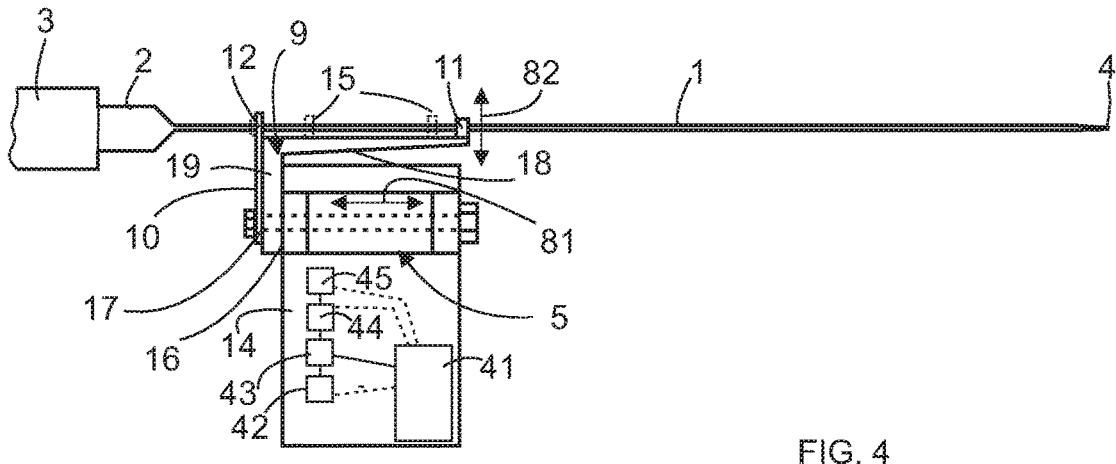
FIG. 4
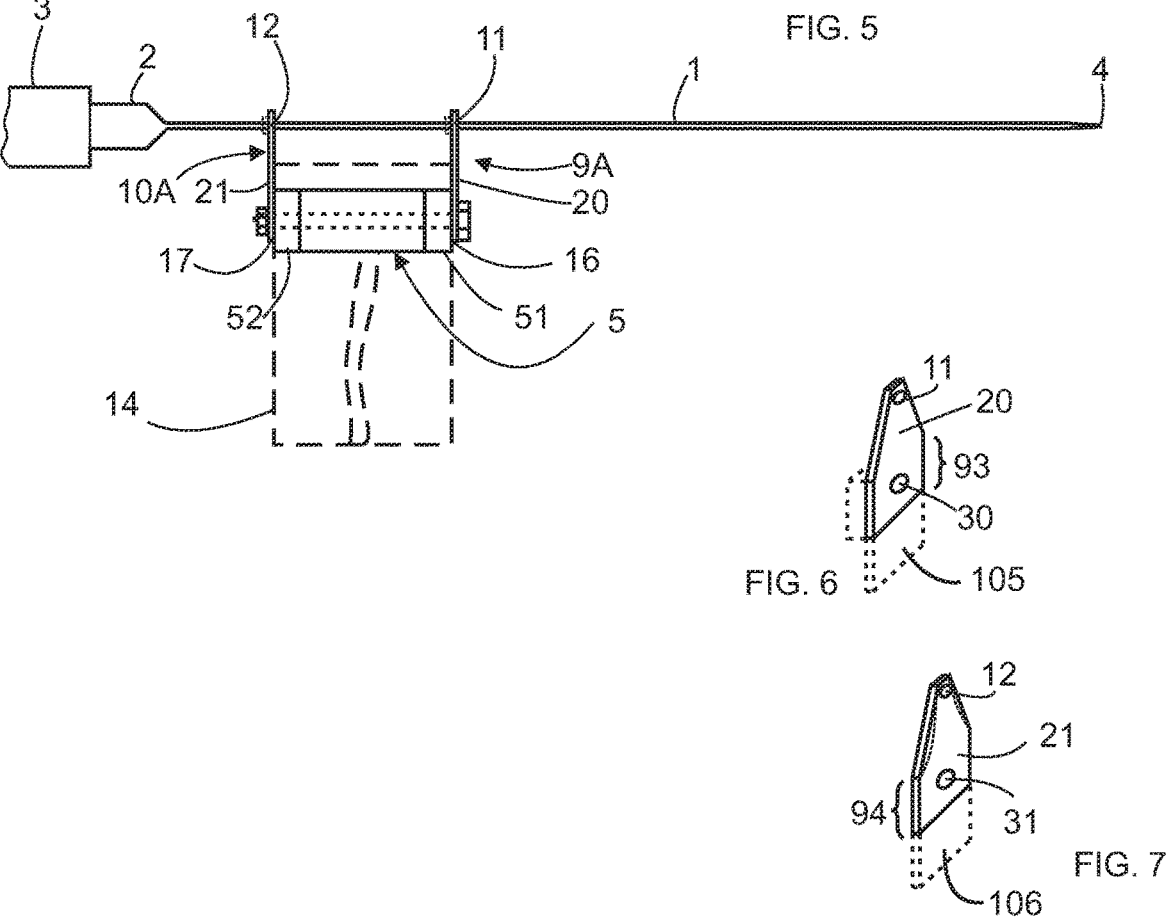
FIG. 5
FIG. 6
FIG. 7

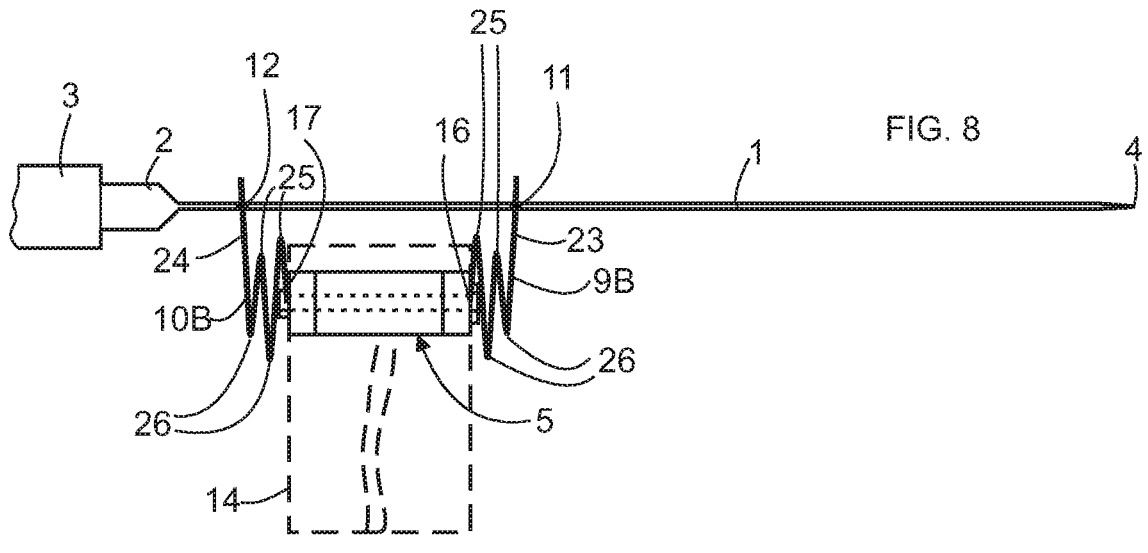
FIG. 8
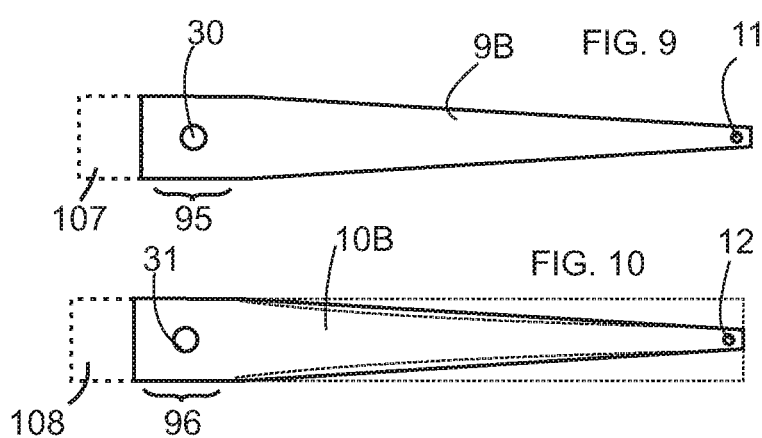
FIG. 9
FIG. 10
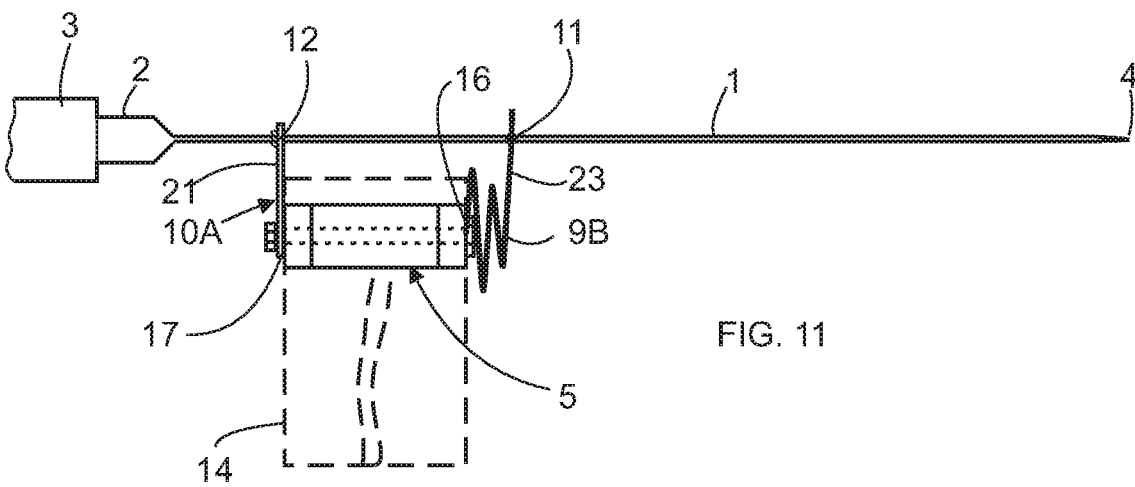
FIG. 11

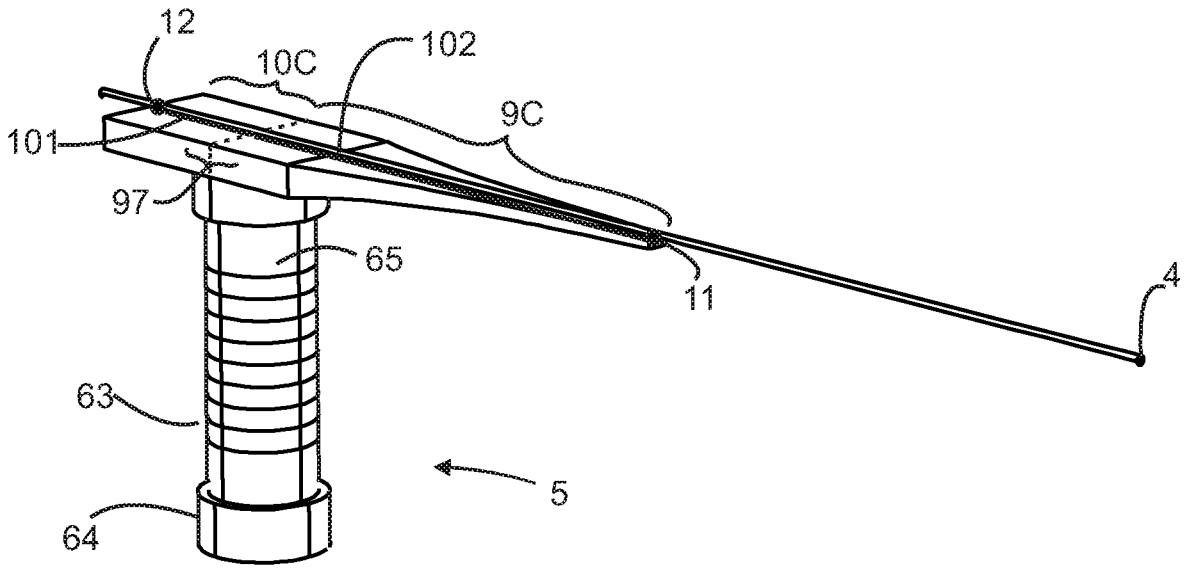
FIG. 12
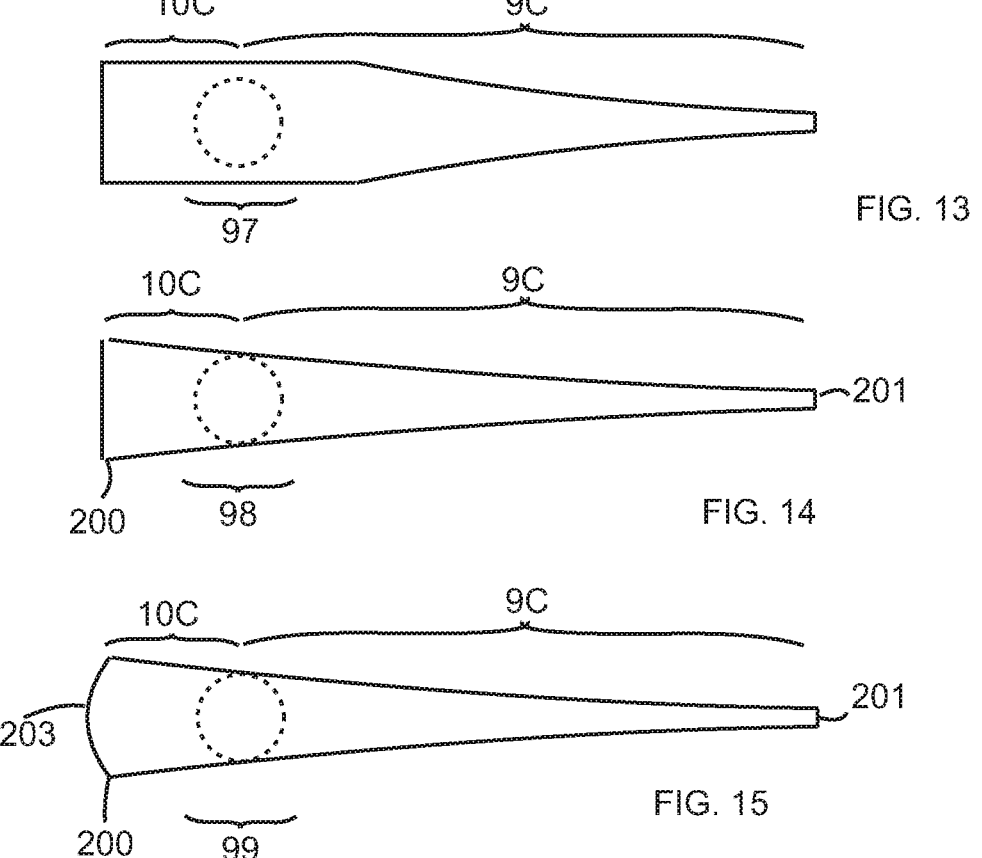
FIG. 13
FIG. 14
FIG. 15

MECHANICAL WAVE INDUCING DEVICE BEING CONNECTABLE TO A NEEDLE

FIELD OF TECHNOLOGY

The invention relates to a mechanical wave inducing device being connected to a needle. The needles are used for medical purpose, e.g. biopsy in order to take samples from a patient's body. Known needle biopsy techniques are for example Fine-Needle Aspiration (FNA) and Core Needle Biopsy (CNB). The mechanical wave inducing device can, for example, comprise an ultrasonic device, an RF source, photo-acoustic, electric spark gap or an electric motor.

PRIOR ART

Needles are broadly employed in medicine, e.g. in drug delivery, surgical procedures and to sample tissue (needle biopsy) or blood. In needle biopsy, to simplify, the tip of the needle is penetrated into the target tissue or the vein of interest, and a syringe, which is attached to the needle is used to provide a low pressure in the needle in order to suck a part of the tissue or fluid through the needle for further examination. There are also other techniques to provide the low pressure in the needle such as vacutainers.

The problem of the current biopsy solutions is that amount of the tissue or fluid, which is obtained from the needle, is relatively small. There are solutions wherein this problem has been solved by transmitting energy to the tip of the needle in order to obtain movement at the tip of the needle. In this way the needle tip can be made to move inside the target tissue very rapidly, which extracts or loosens parts of the target tissue or fluid more efficiently than without the transmission of the energy to the tip.

Therefore, more sample material can be obtained from the tissue or fluid. An alternative solution is to increase needle size, but in order to avoid risk for trauma for the patient this is not so desired. Ultrasound can be used for transmitting such energy to the needle tip. WO 2018000102 shows a known embodiment that utilizes ultrasound transmission. Although the solution of this WO publication is appropriate, it is quite large and has connection cables and tubes limiting portability or usability.

SHORT DESCRIPTION

The aim of the invention is to alleviate the problems of the prior art by allowing efficient conversion of electric energy to mechanical energy in a small and, if necessary, in portable size with handheld devices. The frequency of the mechanical waves can, for example, be at the ultrasound range. The aim is achieved by a device described in an independent claim. Dependent claims disclose different embodiments of the invention.

The inventive device is a mechanical wave inducing device being connectable to a needle. The device has a displacement source 5 and an arrangement for a driving signal. The device has at least two wing parts 9, 9A, 9B, 9C, 10, 10A, 10B, 10C, which are in connection with the displacement source 5. Each wing part 9, 9A, 9B, 9C, 10, 10A, 10B, 10C is arranged to be attachable with the needle 1, and each wing part comprises a connection portion 91, 92, 93, 94, 95, 96, 97, 98, 99, through which the wing part 9, 9A, 9B, 9C, 10, 10A, 10B, 10C is in connection with the displacement source 5. The connection portion is a wing part specific or common to the wing parts.

Each wing part with the connection portion is a converter in order to convert longitudinal mechanical wave movement created by the displacement source into transversal mechanical wave movement for the needle 1, where the transversal mechanical wave is defined as a mechanical wave having particle displacement different from the direction of the wave propagation. It is also possible that at least one of said wing parts 9, 9A, 9B, 9C, 10, 10A, 10B, 10C has a section of a tapered form.

The displacement source can produce a longitudinal mechanical movement in the direction of its longitudinal axis in a relatively small space. At least two wings attachable with the needle makes it possible to transmit the mechanical wave efficiently to the needle including control of the direction of the energy propagation within the needle. However, in order to achieve a desired action for biopsy the device should move the needle at an intended direction with respect to the longitudinal axes of the needle, e.g. transversally. In this case, the wing parts convert the longitudinal movement in mechanical displacement source into the transversal movement in the needle with respect to the needle centre axis. The wing parts occupy also relatively small space. The geometries of the wing parts are such that the conversion from the longitudinal movement to the transversal movement makes it possible for efficient transmission of mechanical energy taken into account mechanical wavelengths.

Further, when matching the transversal mechanical waves to the distal part of the needle 1 with at least one wing part, even a higher transmission efficiency rate can be achieved allowing smaller power consumption and therefore, the size of the displacement source can be then miniaturized. The intensity of mechanical waves produced by the mechanical wave displacement source can depend on the volume of the displacement source, for example if the source is a piezo-electric transducer. Therefore, good efficiency of the system in converting electricity to needle tip motion allows to use a smaller displacement source and lower power consumption is practical especially if the system is batterized.

LIST OF FIGURES

In the following, the invention is described in more detail by reference to the enclosed drawings, where FIG. 1 illustrates an example of parts of the inventive device, FIG. 2 illustrates an example of the inventive device, FIG. 3 illustrates an example of the wing part of the inventive device, FIG. 4 illustrates another example of the inventive device, FIG. 5 illustrates yet another example of the inventive device FIG. 6 illustrates another example of the wing part of the inventive device. FIG. 7 illustrates further another example of the wing part of the inventive device, FIG. 8 illustrates further another example of the inventive device, FIG. 9 illustrates an embodiment of a manufacturing component for yet another example of the wing part, FIG. 10 illustrates another embodiment of a manufacturing component for yet another example of the wing part, FIG. 11 illustrates further another example of the inventive device, FIG. 12 illustrates further another example of the inventive device.

FIG. 13 illustrates the wing parts of FIG. 12.

FIG. 14 illustrates an example of the wing parts for the embodiment of FIG. 12, FIG. 15 illustrates another example of the wing parts for the embodiment of FIG. 12.

DESCRIPTION OF THE INVENTION

Figure 16:
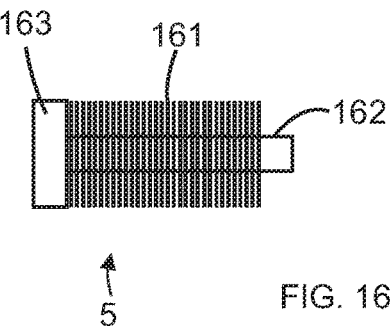
FIG. 16 illustrates another embodiment for the displacement source.

FIG. 1. illustrates an example of parts of the inventive device. FIG. 2 illustrates an embodiment of the invention having the parts shown in FIG. 1. The mechanical wave inducing device according to the invention is connectable to a needle 1. The connection possibilities are described further below. The needle has tip 4 at a distal end of the needle for e.g. puncturing into a target tissue or vein or to achieve another medical function. The proximal end of the needle comprises a connector 2 in order to connect the needle for a low pressure source 3, e.g. a syringe or a vacutainer. Other low pressure sources can also be used.

The device has a displacement source 5 and an arrangement for a driving signal. In the example of FIG. 2 the driving signal arrangement comprises a driving signal connection part 6 in order to connect the displacement source to a signal source. The driving signal connection part 6 comprises an input connector 7 and connecting lines 8 between the input connector 7 and the displacement source. The connecting lines 8 can be wires or rigid lines for example. The input connector 7 can be connected with a cable 13 in order to the transmit the driving signal from a driving signal generator (not shown) to the displacement source 5 via the connection part 6.

The driving signal generators as such are known, and they are used to provide a driving signal that has a desired waveform (e.g. shape, pulse/burst/continuous, envelope, pulse repetition rate) and power. A suitable waveform and power depend on the displacement source used, the other parts (shape and material parameters such as shape, structure, density and mechanical properties) of the inventive device, the structure of the needle 1 and the target tissue. Different tissues and tissue pathologies have different mechanical, structural and compositional properties and may require different needles and different waveforms to be used. So, several parts of the invention and the form and power of the driving signal affect how efficiently the mechanical wave is transmitted to the needle tip in order to move the tip.

The device has two wing parts 9, 10, which can be made of same or different pieces and that are connected to the displacement source 5. FIGS. 1 and 2 show embodiments having two separate wing parts, but it is possible that the wing parts belong to the same piece. So when referring to the embodiment of FIG. 2 the wing parts 9, 10 can be manufactured such that they can be parts of one piece.

Each wing part 9, 10 is arranged to be attachable with the needlel. The examples of FIGS. 1 and 2 comprise connection points 11, 12 to be attached with the needle 1.

Further, each wing part comprises a connection portion 91, 92 (See FIG. 3.), through which the wing part 9, 10, is in connection with the displacement source 5. The connection portion can be wing part specific or common to the wing parts. The common connection portion is convenient when the wing parts are manufactured to be parts of one piece.

The wing parts with the connection portion/s are also converters in order to convert longitudinal mechanical wave movement created by the displacement source 5 into transversal mechanical wave movement of the needle 1. Further, as can be seen on the figures, at least one of the wing parts has a section of a tapered form.

As said above, the displacement source produces a longitudinal mechanical movement in the direction of its longitudinal axis in a relatively small space. In order to have a compact structure, which is easy and convenient to use by a user, the displacement source can be located in parallel with the needle, so the longitudinal axes of the needle and the displacement source can be parallel as can be seen in the figures. On the other hand the displacement source can also be located transversally with respect to the needle as shown in the example of FIG. 12.

In inventive embodiments having connection point, like in FIGS. 1 and 2, at least one connection point can be designed to match the transversal mechanical waves to the needle 1. In this way the power can be transmitted relatively efficiently to the needle with minimized reflection of the wave back towards the displacement source One wing part or the both wing parts 9, 10 can be used for transmitting the mechanical waves to the needle 1. Therefore the mechanical movement created by the displacement source can be transmitted efficiently to the needle. Also one connection point or the both connection points 11, 12 can be designed to match the mechanical waves to the needle. However, it is also possible that one of the connections points is designed to mismatch mechanical waves to the needle. The mismatching connection point 12 is situated at the side of the proximal end of the needle 1, and it has been discovered that it limits (at least mostly) the mechanical waves in the needle to propagate towards the proximal end of the needle. The mismatching connection point tends also to reflect waves coming from the direction of 11 towards 12, towards the tip of the needle 4. Instead of using the connection point 11, 12 (a spot like connection), a long connection area along the needle (a stripe like connection) can be used, as illustrated in the example of FIG. 12. The connection area can also be designed to match or mismatch the mechanical waves.

A mechanical wave in a structure can be achieved, for example, using an ultrasound device, wherein the propagating waves transmitting energy in the structure move in the ultrasound range from 20 kHz up to several gigahertz. An ultrasound device can be, for example, a piezo electric device like Langevin transducer, an RF source, electric spark gap, a photoacoustic device or a small electric motor. It should be noted that other techniques and frequency ranges may also be used than the ultrasound technique. For example devices that create frequencies greater than 0.1 Hz can be used, like air pressure devices or small electric motors. In order for the mechanical wave to propagate properly through interfaces of components, mechanical wave impedances of the components, e.g. the needle and wing part, should be similar or at least close to each other. It can be said that the mechanical wave impedance is the ratio of stress applied to component to velocity of the wave in the component. If the impedances of the components differ significantly reflections of the mechanical waves may occur and the waves do not propagate properly between the components. Therefore, materials of the component in the view of the mechanical wave impedances would be practical to be as close as possible in order to provide a good wave propagation through the interfaces, if necessary. An alternative solution is to use an intermediate layer between the components for matching the impedances of the components as close to each other as possible.

A mechanical wave inducing device comprises a body part 14 that can comprise the displacement source 5 and the driving signal connection part 6 as shown in FIG. 2. The body part provides an installation frame for the parts of the device and also a grip for a user of the device. So, the device can be hand-held.

The connection points 11, 12 (or the connection areas) can be fixed, in which case the needle and device forms one product. Therefore, the connection/s 16, 17 between the wing part/s 9, 10 and the displacement source 5 can also be fixed. However, it is also possible that the connections 16, 17 between the wing part/s 9, 10 and the displacement source 5 can also be detachable. Further, alternative embodiments are that the connection points 11, 12 are detachable, in which case the needle can be disposable.

FIGS. 1 and 2 shows an example of a mechanical wave inducing device wherein one of the wing parts 9 comprises a sub part 18 of the wing 9 and a bar 19, the bar being in a transversal direction with respect to a longitudinal axis 5A of the displacement source 5. FIG. 3 shows the wing part 9 of this example, and also illustrates the other wing part 10. The bar 19 comprises the connection portion 92, which is in connection with the displacement source 5. the sub part 18 of the wing part 9 is in a transversal direction with respect to the bar 19, and has said tapered form with a wide end 18A and a narrow end 18B. The narrow end has the connection point 11 (or connection area) to match the mechanical waves to the needle 1, and the wide end 18A is connected to the bar 19.

If the wing parts 9, 10 belong to one piece, the bar 19 and the connection portion 92 are common with the other wing part 10 and the wing part 9 having said sub part 18. If the wing parts 9, 10 are different pieces as illustrated in FIG. 3, the other wing part 10 is a second bar situated in parallel with the bar 19, and having the other connection point 12 for the needle 1, and also the connection portion 91. A tapered shape of the wing part 9, more precisely the sub part 18 of the wing 9, increases the energy density of the mechanical wave towards the connection point 11.

As said, at least one of the connection points 11, 12, or connection areas matches with respect to the mechanical waves, so the connection point matches the mechanical wave impedances of the needle 1 and the wing part. In the examples of FIG. 1-3 at least the connection point 11 or connection area, which is closer to needle tip is designed to match the mechanical waves to the needle. The other connection point 12 or connection area can be designed to mismatch the mechanical waves, which limits the propagation of the mechanical waves towards the proximal end of the needle 1, i.e. towards the low pressure source 3. Preventing propagation of the mechanical wave preserves the connection hub for unnecessary exposure of the said waves, e.g. protecting the operator from obtaining mechanical wave exposure, protecting the sample obtained or protecting the needle hub from unnecessary stresses or breakage.

The connection point 11 12, or connection area can be made in many ways, like using crimps, solder joints and adhesive (e.g. glue). The figures show schematically the connections points, so in practice they differ from the figures.

FIG. 3 shows also a hole 30 that is used to connect the wing part/s with the displacement source 5. In addition, the device may comprise at least one additional connection 15 with the needle. The additional connection can be useful for example to manufacture an inventive product.

The wing part 9 having a section of a tapered form is located on one side with respect to the displacement source 5 as shown in FIG. 2. In addition, it is possible that there is a wing part 103 that is directed to an opposite side with respect to the displacement source 5. The wing part 103 directed on the opposite side of the displacement source than the wing part having the tapered form tends to increase the efficiency of the mechanical wave energy transmission towards the connection point 11 or connection area. This applies to other embodiments of the invention as well. As can be noted the other wing part 10 may also comprise a wing part 104 directed to the opposite side with respect to the displacement source 5.

FIG. 3A discloses a further embodiment wherein the other wing part 9 comprises a projection 10AC on the other side of the other connection point 12 than the displacement source 5. FIG. 3A shows also an embodiment of the projection in dashed lines, if the wing parts 9, 10 belong to one piece, more precisely the part 10 and the bar 19. The projection 10 AC works as a counterweight in relation to the other connection point 12. The projection can increase a torque effect, which can lead to a better wave transmission. Therefore, the effect at the needle tip can be improved. As can be seen in FIG. 3A the wing parts 9, 10 can be formed separately or as a common part. Further the length of the projection can vary, depending on the design of an embodiment.

FIG. 2 illustrates also the conversion of the longitudinal mechanical wave movement into transversal mechanical movement. The longitudinal mechanical wave 81 created by the displacement source 5 moves the wing parts 9, 10. Since the wing parts have a transversal structure comprising the connection portion 92, 91 with respect to the centre axes of the displacement source 5, they convert the longitudinal mechanical wave movement into the transversal mechanical wave movement 82 with respect to the needle.

FIG. 4 shows another embodiment wherein a battery 41, a control interface 42, a controller 43, a signal generator 44 and an amplification unit 45 are situated in the body part 14. In this way an external signal source, power source and other parts are not needed. There the cable 13 is connecting the displacement source 5 and amplification unit 45, but the input connector 7 is not needed. FIGS. 2 and 4 show different embodiments the inventive device could be manufactured. It is worth to note that the examples of FIGS. 2 an 4 are not only solutions, but the inventive device can be made in other ways as well, for example having no internal power source 41 in the embodiment of FIG. 4, but having an external power course that is connectable to the device.

A battery 41 can be connected with the controller 43 that distributes power for the other parts in the body part. The battery can also be connected directly (dashed lines in FIG. 4) with all parts in order to distribute power. It is convenient that the battery can be recharged when needed. The control interface can, for example, be a display, touchscreen, button/s, thumbwheel etc. so that a user can control the device. The controller 43 controls the operation of the device, being for example a digital signal processor. The signal generator 44 generates an electric drive signal that is transmitted to the displacement source 5. The transmission is made via the amplifier 54 that amplifies the driving signal to have a desired power. Connections can be made through circuits and the controller to obtain information from displacement source 5 performance regarding mechanical wave motions within the system to automatically change parameters of the signal generator 44. Example of such process is measuring optimal resonance frequency of the system or maximizing electric output power from amplifier unit 45.

FIG. 5 shows another embodiment of the inventive mechanical wave inducing device wherein the device has two wing parts 9A, 10B, and one of the wing parts 9A comprises a front bar 20, the front bar being in a transversal direction with respect to a longitudinal axis 5A of the displacement source 5. The front bar 20 comprises a connection portion 93 being connected to a front part 51 of the displacement source 5 and the front bar 20 having one of said connection points 11. The other wing part 10A comprises a rear bar 21, the rear bar being also in a transversal direction with respect to the longitudinal axis 5A of the displacement source 5, The rear bar 21 comprises the connection portion 94 and is connected to a rear part 52 of the displacement source 5 and has the other of said connection points 12.

FIGS. 6 and 7 illustrates the front bar 20 and the rear bar 21. As already said, the bars can be tapered. The tapered shape can be made in many ways, as shown by the dashed lines in FIG. 7. FIGS. 6 and 7 show also connection holes 30, 31 for the displacement source. Further, FIG. 6 illustrates by using the dashed lines that the bar can be fixed with front part of the displacement source (also possible with the rear part). The front and rear bars, i.e. the wing parts may also comprise a further wing 105, 106 directed on the opposite side of the displacement source than the wing part having the tapered form as illustrated in FIGS. 6 and 7. The bars can also have a rectangular shape as illustrated in FIG. 3. They can also vertically widen along the structure towards 12, if acoustic mismatch is intended to be pronounced.

FIG. 8 shows a further example of a mechanical wave inducing device according to the invention. For maximum displacement at the tip of the waveguide (wing part), the rate of tapering can be limited. A long waveguide can thus be folded to make the waveguide fit into a small volume.

At least one wing part 9B has a folded structure, the tapered shape, and also having an extension element 23, the extension element is approximately in a transversal direction with respect to a longitudinal axis 5A of the displacement source 5, and the extension element has one of said connection points 11.

FIG. 11 shows another embodiment of this structure. In the embodiment of FIG. 11 the other of the wing parts 10A has a bar form 21 having the connection portion 94 the other connection point 12. This wing part 10A can also be rectangular or diverging upwards.

In the embodiment of FIG. 8 the other of the wing parts 10B has also a folded structure and a tapered shape, and also a second extension element 24. The second extension element is also in the transversal direction with respect to a longitudinal axis 5A of the displacement source 5, and the second extension element has the other connection point 12. In case of resonant waves, if desired, it is possible that the folded structure or structures 9B, 10B can be designed to locate nodes of the mechanical waves induced by the displacement source 5 to peaks 25 and troughs 26 of the folded structure or structures.

It is also possible in the embodiments of FIGS. 8 and 11 that the connection point 11 of the wing part 9B having said folded structure is designed to match mechanical waves to the needle 1, and the other connection point 12 of the bar form wing part 21 or the other folded structure 10B is designed to mismatch mechanical waves to the needle 1.

FIGS. 9 and 10 show the folded wing parts without folding, i.e. as straight prefabricated components, when the tapered form the wing parts can be seen clearly. FIGS. 9 and 10 illustrates also the common connection portion 95, 96. The tapered shape provides a good wave propagation and promotes also the mechanical wave matching with the needle. There can be many different tapered shapes as illustrated in FIG. 10. A flat end of a rectangular form can be used if the mechanical wave mismatching is desired. Alternatively, the structure 10 can be wider at mismatching point 12 than the width near 5A. When using folded wing parts, i.e. waveguides, the mechanical wave matching with the needle can be achieved conveniently in a compact space. As can be noted in FIGS. 9 and 10, the wing part 9B, 10B may also comprise a wing 107, 108 at the opposite direction than the tapered part with respect to the common connection portion 95, 96.

In one embodiment the connection point 11 of the wing part 9B having said folded structure is designed to match mechanical waves to the needle 1, and the other connection point 12 of the bar form wing part 21 is designed to mismatch mechanical waves to the needle 1. As said, the folded structure 9B, 10B can be designed to locate nodes of the mechanical waves induced by the displacement source 5 to peaks 25 and troughs 26 of the folded structure.

FIG. 12 shows yet another example of the invention how the invention can be provided. In this embodiment the device has two wing parts 9C, 10C having the common connection portion 97. The both wing parts, 100, 9C are in a transversal direction with respect to a longitudinal axis 5A of the displacement source 5, and having a common longitudinal axis, the both wing parts being directed to opposite directions on along the common longitudinal axis. The common connection portion 97 connects the wing parts to the displacement source 5. The displacement source 5 can be situated in the body part 14 although not shown in FIG. 12.

The both wing parts 10C, 9C has a shaft like form, the first wing part 9C having a tapered form with a wide end and a narrow end. The narrow end having said connection point 11, and the wide end comprising a part of said connection portion 97. The second wing part 10C has the other connection point 12 and another part of said connection portion 97.

The connection point 11 at the narrow end of the tapered form can be arranged to match the mechanical waves to the needle 1. The connection point 12 at the second wing part 100 can be arranged to mismatch the mechanical waves to the needle 1.

FIG. 12 shows also another embodiment of the invention. In this embodiment the device has also two wing parts 9C, 10C having the common connection portion 97, the both wing parts, 100, 9C being in a transversal direction with respect to a longitudinal axis 5A of the displacement source 5, and having a common longitudinal axis. The both wing parts being directed to opposite directions along the common longitudinal axis.

The both wing parts 100, 9C has a shaft like form, the first wing part 9C having a tapered form with a wide end and a narrow end, the wide end comprising a part of said connection portion 97. Instead of having the connection point, the first wing part 9C has also one connection area 102, and the second wing part 100 has the other connection area 101 and also another part of said connection portion 97.

The connection areas 101, 102 have a stripe like form. The length of the stripe like connection can be designed to be suitable with other structures of the device like, the needle size and the shape of the wing part. The connection areas 101, 102 of the wing parts may also be so long that they are in connection with each other and reach points 11 and 12.

FIG. 13 shows the wing parts 9C, 10C of the embodiments of FIG. 12 and the common connection portion 97 viewing form another angle. The displacement source is illustrated as a dashed line circle.

FIG. 14 shows another embodiment and the common connection portion 98 wherein first wing part 9C and the second wing part 100 form an integral structure, which is tapered from end 200 to end 201 of the structure, in such a way that the narrow end 201 is at the end of the first wing part 9C and the end of the second wing part 10C provides a wide end 200 of the tapering.

FIG. 15 shows yet another embodiment and the common connection portion 99 wherein first wing part 9C and the second wing part 100 form an integral structure, which is tapered from end 200 to end 201 of the structure, in such a way that the narrow end 201 is at the end of the first wing part 9C and the end of the second wing part 10C provides a wide end 200 of the tapering, and an end face 203 of the wide end is curved.

Figure 17:
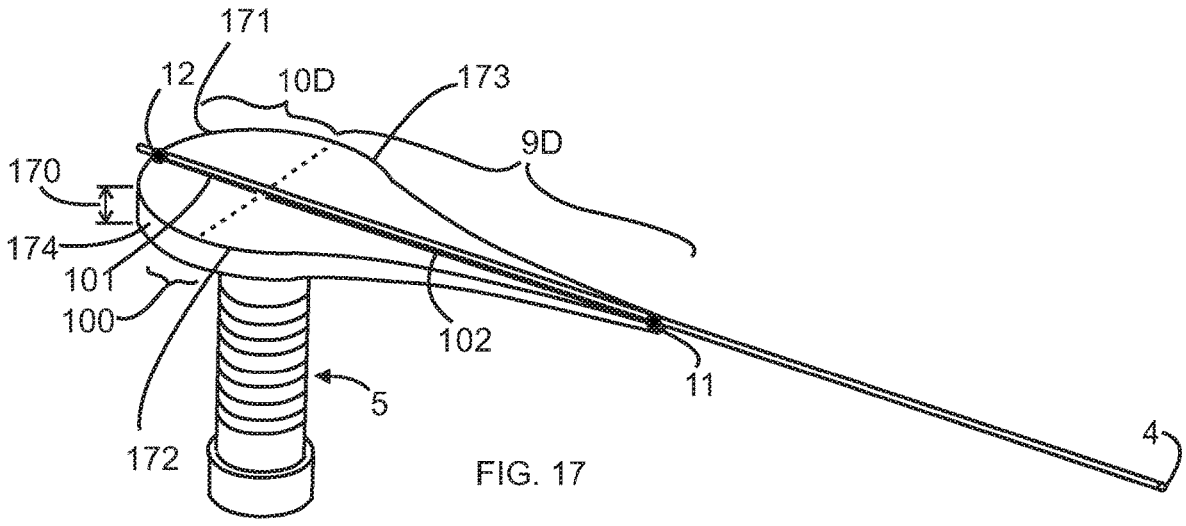
FIG. 17 illustrates further another example of the inventive device.

FIG. 17 shows further example of an embodiment of the invention wherein the device has also two wing parts 9D, 10D having the common connection portion 100, the both wing parts, 10D, 9D being in a transversal direction with respect to a longitudinal axis 5A of the displacement source 5, and having a common longitudinal axis. The both wing parts being directed to opposite directions along the common longitudinal axis.

The first wing part 9D has a tapered form with a wide end and a narrow end, the wide end comprising a part of said connection portion 100. The wide end is based on a form of semi-circle from where the first wing part tapers towards narrow end, for example in a parabolic way. The second wing part 10D has also the semi-circle form, so the semi-circles of the wing parts 9D, 10D form a circle, which provides the connection portion. The circle form can be employed to direct the reflections of the mechanical waves (like ultrasound waves) in the structure towards the centre of the circle, and the narrow end of the first wing part 9D towards the needle tip 4. Therefore, the energy of the mechanical way can be directed towards the needle tip. The height 170 of the edge of the circle can be the same, lower or higher than the height at the center area of the circler (i.e. at the connection portion). So, the wing parts may thin towards the edges. The structure of FIG. 17 can have the connection points 11, 12 or the connection areas 102, 101 as well.

Figure 18:
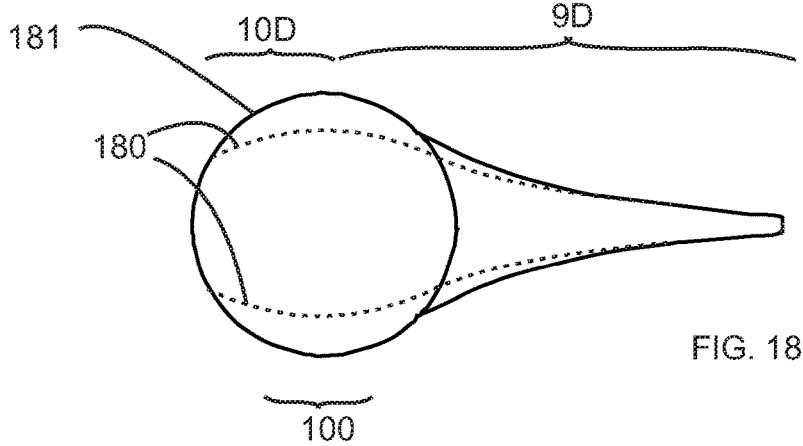
FIG. 18 illustrates an example of the wing parts for the embodiment of FIG. 17.

FIG. 18 shows yet another embodiment of the structure of FIG. 17 having the common connection portion 100 wherein first wing part 9D and the second wing part 10D form an integral structure. Instead of the circle 181 form provided by the first wing part 9D and the second wing part 10D, the form can be another curved form 180, which can be more near the form of an ellipse or parabolic, like FIG. 18 illustrates using the dashed lines. In this way a compact structure can be manufactured. As can be noted above the common curves may provide parts of a circle, parts of an elliptic shape, parts of a parabolic shape or even other shapes.

So, regarding the examples of FIGS. 17 and 18, the first wing part 9D having the tapered form with the wide end and the narrow end, the wide end comprises a part of said connection portion (100). The side edges of the wide end can be in a form of a curve 172, 173, like a section or a part of a circle or another curved shape. The side edges 171, 174 of the second wing part (10D) can also be in the form of the curve form. The curves 171, 174, 172, 173 of the side edges of the wing parts 9D, 10D perform common curves at both sides, and the connection portion 100 is between the common curves (curve 171, 174 at one side and curve 172, 173 at another side). So, the common curves can provide parts of a circle. Since the curves at both sides integrate at the end of the second wing part 10D, they provide an integral curved edge that FIG. 18 clearly illustrates.

In the examples of FIGS. 1 and 2 the displacement source 5 is an ultrasound device having a transducer 62. The transducer comprises a piezoelectric module 63, a front part 64, a back part 65 and a bolt 66 connecting the piezoelectric module. The bolt connects the front part and the back part together in such a way that the piezoelectric module is between the front part and the back part. An ultrasound device has been found to be a convenient displacement source, but other solutions can be used as well. In practice, the front part 64 and back part 65 are mechanically, like acoustically, conducting and electrically isolating.

The displacement source can also be a solenoid 161 and its core structure 162 that is connected to an acoustic horn structure 163 for producing, for example ultrasound energy, see FIG. 16. The driving signal is connected to the solenoid 161, which in turn transmits the electric energy via the electromagnetic field to a core structure 162, which, as said, is connection with the acoustic horn. The core structure moves as response to the changes of the electromagnetic field, and the movements of the core structure moves the acoustic horn.

It is said in the above example that at least a part of the wing part in a transversal direction with respect to a longitudinal axis 5A of the displacement source 5. It should be note that in this text the term transversal is not restricted to be perpendicular, but also covering other angles as well. A practical embodiment is that an angle range is around the right-angle between the displacement source and the wing part (or its part), let's say 20 degrees on the both sides of the middle (the right-angle) of the range.

As can be noted the inventive mechanical wave inducing device comprises an arrangement for a drive signal that can be formed in many ways. The arrangement for a driving signal can comprise a driving signal connection part 6 in order to connect the displacement source to a signal source as shown in FIG. 2. The other arrangement for a driving signal as shown in FIG. 4 can comprise a battery 41, a control interface 42, a controller 43, a signal generator 44 and an amplification unit 45 in the body part 14.

The inventive device is used for moving the needle tip. The invention can be used with the needles that are used in biopsy including techniques like Fine-Needle Aspiration (FNA) and Core Needle Biopsy (CNB). It is also worth of noting that invention can be used with so called painless needles as well. The movement of the needle tip can alleviate the pain experience when puncturing the needle into the target tissue or contribute to cell, drug, genetic material delivery into organs, tissue or cells.

It is worth mentioning that the mechanical waves, longitudinal or transversal, can be standing waves or travelling waves. The standing waves refers to waves when they resonate in a structure, in which cases the peaks and the displacement nodes of the wave typically are located at specific positions. The travelling waves refers to waves that appears to travel, e.g. the displacement peaks move. Further, it is worth mentioning that the material displacement in the longitudinal waves occur within the same direction the mechanical waves are travelling. The material displacement of the transversal waves occurs transversally as compared to the direction of the travelling wave.

As can be seen from the examples illustrated above, the inventive device can be made in many ways. For example, the wing parts can be made in multiple ways. The invention may also be used to achieve atomization or nebulization. Atomization or nebulization can be achieved e.g. by selecting frequency and displacement amplitudes so that capillary waves on the liquid droplet surface or cavitation within the droplet are generated. Different needles can be used for different tissue types or pathologies; therefore, different inventive embodiments can be made in order to provide a properly functioning device.

It is evident from the above that the invention is not limited to the embodiments described in this text but can be implemented in many other different embodiments within the scope of the independent claims.

The invention claimed is:

1. A mechanical wave inducing device being connectable to a medical needle, the device having a displacement source and an arrangement for a driving signal, at least two wing parts, which are in connection with the displacement source,
   and which each wing part is arranged to be attachable with the needle, and
   which each wing part comprises a connection portion, through which the wing part is in connection with the displacement source, the connection portion being common to the wing parts,
   said each wing part with the connection portion being a converter in order to convert longitudinal mechanical wave movement created by the displacement source into transversal mechanical wave movement for the needle, two of the wing parts being directed to opposite directions with respect to the connection portion;
   wherein each wing part has a respective stripe-like connection area and each wing part is arranged to be attachable with a different part of the needle's length via its respective stripe-like connection area.

2. The mechanical wave inducing device according to claim 1, wherein at least one of said wing parts has a section of a tapered form.

3. The mechanical wave inducing device according to claim 2, wherein the device comprises a body part that comprises the displacement source and the arrangement for the driving signal.

4. The mechanical wave inducing device according to claim 3, wherein the connection areas are fixed.

5. The mechanical wave inducing device according to claim 4, wherein at least one connection between said at least one connection portion and the displacement source is detachable.

6. The mechanical wave inducing device according to claim 3, wherein at least one connection between said at least one connection portion and the displacement source is fixed.

7. The mechanical wave inducing device according to claim 3, wherein the connection areas are detachable.

8. The mechanical wave inducing device according to claim 7, wherein the at least one connection between said at least one connection portion and the displacement source is detachable.

9. The mechanical wave inducing device according to claim 7, wherein the at least one connection between said at least one connection portion and the displacement source is fixed.

10. The mechanical wave inducing device according to claim 1, wherein the connection areas are designed to match the transversal mechanical waves to the needle.

11. The mechanical wave inducing device according to claim 1, wherein said mechanical waves are standing waves or travelling waves.

12. The mechanical wave inducing device according to claim 11, wherein one of the connection areas is designed to mismatch mechanical waves to the needle.

13. The mechanical wave inducing device according to claim 1, wherein at least one of said wing parts has a section of a tapered form located on one side with respect to the displacement source, and one of the wing parts is directed to an opposite side with respect to the displacement source.

14. The mechanical wave inducing device according to claim 1, wherein the arrangement for a driving signal comprises a driving signal connection part in order to connect the displacement source to a signal source.

15. The mechanical wave inducing device according to claim 1, wherein the arrangement for a driving signal comprises a battery, a control interface, a controller, a signal generator and an amplification unit in the body part.

16. The mechanical wave inducing device according to claim 1, wherein the device has two wing parts having a common connection portion, the both wing parts, being in a transversal direction with respect to a longitudinal axis of the displacement source, and having a common longitudinal axis, the both wing parts being directed to opposite directions on along the common longitudinal axis,
the both wing parts having a shaft like form, the first wing part having a tapered form with a wide end and a narrow end, the narrow end having a connection point, and the wide end comprising a part of said common connection portion, and the second wing part having another connection point and another part of said common connection portion.

17. The mechanical wave inducing device according to claim 16, wherein a connection point at the narrow end of the tapered form is arranged to match the mechanical waves to the needle.

18. The mechanical wave inducing device according to claim 17, wherein a connection point at the second wing part is arranged to mismatch the mechanical waves to the needle.

19. The mechanical wave inducing device according to claim 16, wherein the first wing part and the second wing part form an integral structure which is tapered from end to end of the structure, in such a way that the narrow end is at the end of the first wing part and the end of the second wing part provides a wide end of the tapering.

20. The mechanical wave inducing device according to claim 16, wherein first wing part and the second wing part form an integral structure which is tapered from end to end of the structure, in such a way that the narrow end is at the end of the first wing part and the end of the second wing part provides a wide end of the tapering, and an end face of the wide end is curved.

21. The mechanical wave inducing device according to claim 20, wherein the wing parts thin towards the edges.

22. The mechanical wave inducing device according to claim 1, wherein the device has two wing parts having the common connection portion, the both wing parts, being in a transversal direction with respect to a longitudinal axis of the displacement source, and having a common longitudinal axis, the both wing parts being directed to opposite directions along the common longitudinal axis,
   the both wing parts having a shaft like form, the first wing part having a tapered form with a wide end and a narrow end, the wide end comprising a part of said connection portion, the first wing part having also one connection area, and the second wing part having the other connection area and another part of said connection portion.

23. The mechanical wave inducing device according to claim 1, wherein the device has two wing parts having the common connection portion, the both wing parts, being in a transversal direction with respect to a longitudinal axis of the displacement source, and having a common longitudinal axis, the both wing parts being directed to opposite directions on along the common longitudinal axis, the first wing part having a tapered form with a wide end and a narrow end, the wide end comprising a part of said connection portion, side edges of the wide end being in a form of a curve, side edges of the second wing part being also in the form of the curve form, the curves of the side edges of the wing parts performing common curves, the connection portion being between the curved parts, and the narrow end of the first wing part having said connection point, and the second wing part having the other connection point and another part of said connection portion.

24. The mechanical wave inducing device according to claim 23, wherein the connection point at the narrow end of the tapered form is arranged to match the mechanical waves to the needle.

25. The mechanical wave inducing device according to claim 24, wherein the connection point at the second wing part is arranged to mismatch the mechanical waves to the needle.

26. The mechanical wave inducing device according to claim 23, wherein the common curves provide parts of a circle, parts of an elliptic shape or parts of a parabolic shape.

27. The mechanical wave inducing device according to claim 1, wherein the device has two wing parts having the common connection portion, the both wing parts, being in a transversal direction with respect to a longitudinal axis of the displacement source, and having a common longitudinal axis, the both wing parts being directed to opposite directions on along the common longitudinal axis, the first wing part having a tapered form with a wide end and a narrow end, the wide end comprising a part of said connection portion, side edges of the wide end being in a form of a curve, side edges of the second wing part being also in the form of the curve form, the curves of the side edges of the wing parts performing common curves, the connection portion being between the curved parts, and the narrow end of the first wing part having said connection area, and the second wing part having the other connection area and another part of said connection portion.

28. The mechanical wave inducing device according to claim 1, wherein the displacement source is an ultrasound device having a transducer, the transducer comprises a piezoelectric module, a front part, a back part and a bolt connecting the piezoelectric module, the front part, and the back part together in such a way that the piezoelectric module is between the front part and the back part.

29. The mechanical wave inducing device according to claim 1, wherein the displacement source is a solenoid and its core structure, which core structure is connected to an acoustic horn structure, the solenoid being connected to the arrangement for the driving signal, and the solenoid being arranged to transmit the electric energy via the electromagnetic field to a core structure being connected to the acoustic horn structure.

30. The mechanical wave inducing device according to claim 1, wherein the displacement source is an electric spark gap, an air pressure device or an electric motor.

* * * * *